(12) United States Patent
Alfano et al.

(10) Patent No.: US 11,614,398 B2
(45) Date of Patent: Mar. 28, 2023

(54) METHOD FOR IMAGING BIOLOGICAL TISSUE USING POLARIZED MAJORANA VECTOR AND COMPLEX VORTEX PHOTONS FROM LASER AND SUPERCONTINUUM LIGHT SOURCES

(71) Applicant: Robert Alfano, Bronx, NY (US)

(72) Inventors: Robert Alfano, New York, NY (US); Sandra Mamani, White Plains, NY (US); Lingyan Shi, La Jolla, CA (US)

(73) Assignee: Robert Alfano, Bronx, NY (US)

( * ) Notice: Subject to any disclaimer, the term of this patent is extended or adjusted under 35 U.S.C. 154(b) by 0 days.

(21) Appl. No.: 16/990,623

(22) Filed: Aug. 11, 2020

(65) Prior Publication Data

US 2021/0080382 A1 Mar. 18, 2021

Related U.S. Application Data

(63) Continuation-in-part of application No. 16/573,521, filed on Sep. 17, 2019, now Pat. No. 10,733,729.

(51) Int. Cl.
*G01N 21/21* (2006.01)
*G01N 21/47* (2006.01)
(Continued)

(52) U.S. Cl.
CPC ......... *G01N 21/21* (2013.01); *G01N 15/0211* (2013.01); *G01N 21/47* (2013.01);
(Continued)

(58) Field of Classification Search
CPC ..... G06T 7/0012; G01J 9/00; G01J 2004/001; G01J 2004/002; G01J 2004/005;
(Continued)

(56) References Cited

U.S. PATENT DOCUMENTS

| | | | | |
|---|---|---|---|---|
| 6,567,164 B2* | 5/2003 | Birk | ...................... | B82Y 20/00 356/317 |
| 7,408,637 B2* | 8/2008 | Freeling | .................... | G01J 3/02 356/300 |

(Continued)

OTHER PUBLICATIONS

Mamani, Sandra et al., "Transmission of classically entangled beams through mouse brain tissue," 2019, Journal of Biophotonics, pp. 1-6. (Year: 2019).*

(Continued)

*Primary Examiner* — Gordon J Stock, Jr.
(74) *Attorney, Agent, or Firm* — Nolte Lackenbach Siegel; Myron Greenspan

(57) ABSTRACT

A super class of polarized transverse vector vortex photon beams patterns are mathematically represented here, which are *Majorana*-like among them are the radial and azimuthal Laguerre-Gaussian, hybrid π-vector beams, and Airy beams. These optical beams are consider spin-orbit coupled beams based on OAM and SAM parts of light. A *Majorana* photon is a photon that is identical to its anti-photon. It has within itself both chirality, right and left-handed twist in polarization (SAM) and wavefront (OAM). Applications using *Majorana* photons improve optical deeper imaging, higher resolution imaging, Nonlinear Optics effects (SHG, SRS, SC), optical communication in free space and fibers, quantum computer as basic qubit, and entanglement for security.

3 Claims, 6 Drawing Sheets

(51) Int. Cl.
*G01N 15/02* (2006.01)
*G02B 21/36* (2006.01)
*G02B 21/16* (2006.01)
*G01N 33/483* (2006.01)
*G06T 7/00* (2017.01)
*G01N 21/64* (2006.01)
*G01N 15/00* (2006.01)
*H04N 5/372* (2011.01)

(52) U.S. Cl.
CPC ......... *G01N 33/4833* (2013.01); *G02B 21/16* (2013.01); *G02B 21/36* (2013.01); *G06T 7/0012* (2013.01); *G01N 21/64* (2013.01); *G01N 2015/0065* (2013.01); *G01N 2201/06113* (2013.01); *H04N 5/372* (2013.01)

(58) Field of Classification Search
CPC ........ G01J 4/00; G01J 4/02; G01J 4/04; G01J 2009/002; G01J 2009/004; G01N 2021/1765; G01N 2021/216; G01N 2021/218; G01N 33/483; G01N 33/4833; G01N 33/48; G01N 24/00; G01N 21/17; G01N 21/21; G01N 21/23; G01N 21/453; G01N 21/47; G01N 21/64; G01N 15/0211; G01N 2015/0065; G01N 2201/06113; G02B 21/002; G02B 21/16; G02B 21/36; H04N 5/372
See application file for complete search history.

(56) References Cited

U.S. PATENT DOCUMENTS

| | | | | |
|---|---|---|---|---|
| 7,518,127 | B2 * | 4/2009 | von Zanthier | B82Y 15/00 250/492.1 |
| 8,111,957 | B2 | 2/2012 | Alfano et al. | |
| 9,134,300 | B2 | 9/2015 | Danias et al. | |
| 9,350,977 | B1 | 5/2016 | Prasad | |
| 9,557,262 | B2 * | 1/2017 | Zeilinger | G01N 21/636 |
| 9,823,486 | B2 | 11/2017 | Prasad | |
| 10,156,669 | B2 | 12/2018 | Beresna et al. | |
| 10,209,192 | B2 | 2/2019 | Ashrafi | |
| 10,393,643 | B2 * | 8/2019 | Swartzlander, Jr. | G01N 15/1434 |
| 10,401,294 | B2 | 9/2019 | Alfano et al. | |
| 10,733,729 | B2 | 8/2020 | Alfano et al. | |
| 2007/0115551 | A1 | 5/2007 | Spilman et al. | |
| 2014/0371582 | A1 * | 12/2014 | Alfano | A61B 5/0059 600/431 |
| 2017/0049326 | A1 * | 2/2017 | Alfano | G01N 21/359 |
| 2017/0153435 | A1 * | 6/2017 | Alfano | G06N 10/00 |
| 2018/0284025 | A1 * | 10/2018 | Gozali | G01N 21/6458 |
| 2019/0290100 | A1 | 9/2019 | Ramachandran et al. | |
| 2019/0393963 | A1 | 12/2019 | Shi | |
| 2020/0011737 | A1 * | 1/2020 | Shi | G01J 11/00 |
| 2020/0057957 | A1 * | 2/2020 | Johnson | G06N 10/00 |
| 2020/0090329 | A1 | 3/2020 | Alfano | |
| 2020/0287631 | A1 * | 9/2020 | Gimeno-Segovia | G06N 10/00 |

OTHER PUBLICATIONS

Mamani, Sandra et al., "Laguerre-Gaussian Vortex Beam Transmission through Mouse Brain Tissue," 2018, Frontiers in Optics/Laser Science, 3 pages (Year: 2018).*

Henriques, Ricardo et al., "QuickPALM: 3D real-time photoactivation nanoscopy image processing in ImageJ," 2010, Nature Methods, vol. 7, No. 5, pp. 339-340. (Year: 2010).*

Kleele, Tatjana et al., "An assay to image neuronal microtubule dynamics in mice," 2014, Nature Communications, 5:4827, DOI: 10.1038/ncomms5827, www.nature.com/naturecommunications, pp. 1-10. (Year: 2014).*

Van Huizen, Laura M.G. et al., "Second and third harmonic generation microscopy visualizes key structural components in fresh unprocessed healthy human breast tissue," 2019, Journal of Biophotonics, 12: e201800297, https://doi.org/10.1002/jbio.201800297, pp. 1-11. (Year: 2019).*

S. Mamani, D. Nolan, L. Shi, R. Alfano, Special classes of optical vector vortex beams are Majorana-like photons, Optics Communication 464, 125425 (2020).

S. Mamani, L. Shi, D. Nolan, R. Alfano, Majorana vortex photons a form of entangled photons propagation through brain tissue, J. Biophotonics (2019) e201900036.

H. Nielsen, M. Ninomiya, Bosons being their own antiparticle in Dirac formulation, 2015, ArXiv:1510.03932v1.

F. Tamburini, B. Thidé, I. Licata, F. Bouchard, E. Karimi, Majorana states for subluminal structured photons, 2018, arXiv:1707.07160v4.

* cited by examiner

METHOD FOR IMAGING BIOLOGICAL TISSUE USING POLARIZED MAJORANA VECTOR AND COMPLEX VORTEX PHOTONS FROM LASER AND SUPERCONTINUUM LIGHT SOURCES

CROSS-REFERENCE TO RELATED APPLICATIONS

This application claims priority to Provisional Patent Application 62/732,378 (filed Sep. 17, 2018) and Non-Provisional patent application Ser. No. 16/573,521 filed on Sep. 17, 2019, issued as U.S. Pat. No. 10,733,729, the entirety of which is incorporated herein by reference.

BACKGROUND OF THE INVENTION

Photons possess novel salient properties such as polarization, wavelength, coherence, speed, and spatial modes, which can play an important role for propagation and imaging in scattering media. Complex and Structured vector light spatial mode is an active research topic in various fields in classical and quantum entanglement applications. Photons can have unique vector properties which show that certain photons can be entangled locally and non-locally, separable and non-separable on wave front; can also possess spin angular momentum (SAM) and orbital angular momentum (OAM). Light possess two chiral forms: polarization and wavefront.

Due to inhomogeneous make up of tissue from particles and structure, biological tissues are highly scattering media. Tissues possess chiral structures from proteins and molecular arrangements such brain, breast, lung, among others. In this case, the wavelength plays a key role for biological media the scattering reduces as wavelength enters the NIR (650 nm to 950 nm) and in SWIR (1000 nm to 2500 nm). The optimum window in SWIR for deep imaging is the golden window (1600 to 1870 nm) in the brain.

Moreover, photon polarization plays an important role in tissues since it can affect the depth at which the beam travels. For example, it is known that circular polarized light goes deeper than linear polarized light in scattering media. Depending on scattering unit size, the polarization retains optical memory. A Laguerre-Gaussian beam (LG beam), which is a vortex beam, can carry different types of polarization (linear, circular, radial and azimuthal) along with a phase front characterized by an orbital angular momentum (OAM) of l value and spin angular momentum (SAM) S=+/−1. Light beams with spatially inhomogeneous profile of polarization are referred to as vector beams. The various spatial modes, such as the radial and azimuthal, have non-separable parts for circular polarization and OAM. The combination of polarization and spatial modes leads to special class of photons. These quasi particles are the basis proposed here as *Majorana* photons—where photons and antiphotons are the same.

The key characteristic of vector beams such as radial and azimuthal combined polarization and spatial modes, which are non-separable and are locally entangled. The focus of these beams have a longitudinal field. Moreover, the characteristic of non-separability in vector beams is of great interest not just in optical imaging but in optical communication and computers as well since its polarization degree of freedom and spatial mode are being explored to encode information. There are two special vector beams, radial and azimuthal; these two are a mixture of OAM and circular polarization; and are introduced here as *Majorana* modes and interaction in tissue for the first time. There is a search on for special quasi particles for storage and more stable for qubits that are less effected by interference and by the environment to reduce de-coherence effects and scattering.

*Majorana* can exist not only as fermions but also as bosons coincide of particle and antiparticle such as gravitons, photons and possible the neutrino, as they must be their own anti-particle and have opposite charges and same masses. *Majorana* only works for neutral particles. Charge and neutral particles have antiparticles; that is an electron with charge −e, so its antiparticle (the positron has charge of +e). These can not constitute a *Majorana* particle. However, the neutrino can fit, being a *Majorana*. Some have proposed bosons can be photons. Photons have no charge, the *Majorana* involves not only spin angular momentum but the vector sum of total angular momentum J, with OAM(l). Because of the transverse nature of electric (E) and magnetic (B) fields, the photon has zero rest mass. However, if special photons have a longitudinal field then the photon may have a small mass (Procar) on order of 10-49 gm. *Majorana* photons have both chiral twists. The key *Majorana* characteristic wave function feature is being its own anti-particle, where $\psi=\psi^*$, being Hermitian. This *Majorana* as qubit of this type is topological which means its property remains almost the same regardless of the scattering exchange and the path taken in environment such as scattering. The Fourier transform of a pulse at $\omega_o$ of duration $\tau_p$ in the time domain transforms mathematically into frequency domain signals centered at $\omega_o$ and $-\omega_o$. Typically in an Optics course, one can drop the negative frequency $-\omega_o$ as being physically not real. However, this is not totally correct. The negative frequencies of photons mean negative energy E=hv exactly what Dirac found when he completed solving relativistic quantum mechanics equations and found anti-electrons and anti-particles. Later, positron was found. Experimentally Ettore Majorara proposed a neutrino as being a particle being its own anti particle. *Majorana* neutrinos have the property that the neutrino and antineutrino could be distinguished only by chirality. If experiments observe a difference between the neutrino and antineutrino could simply be due to one particle with two possible chiralities. It is still not yet known whether neutrinos are *Majorana* or Dirac particles; photons do possess chirality in from of vector beams.

The discussion above is merely provided for general background information and is not intended to be used as an aid in determining the scope of the claimed subject matter.

SUMMARY OF THE INVENTION

*Majorana* photons are transmitted through a biological tissue sample to image the tissue. The *Majorana* photons have a circular polarization, a radial polarization or an azimuthal polarization. The transmitted photons are processed to produce a digital image of the biological tissue sample.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
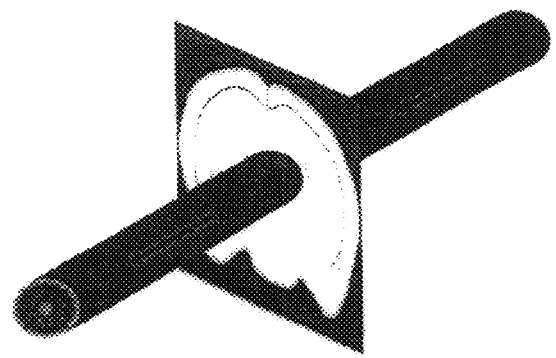
FIG. 1 shows a *Majorana* radially polarized beam going through a mouse brain slide.

This disclosure pertains to certain vector class of photons being a *Majorana*, a combination of particle and antiparticles such these photon modes are defined and attributed as *Majorana* boson photons stated as shown to be $\psi=\psi^*$. The photon and the anti-photon are identical. Some beam possesses both right and left circular polarization.

This disclosure focuses on the transmission of these *Majorana* LG vector vortex beams through mouse brain tissue. The regimes that are disclosed are in the ballistic ($z<l_{tr}$) and diffusive ($z>l_{tr}$) regions, where z is the thickness of the turbid media and $l_{tr}$ is the transport mean free path. Different types of polarizations at different special locations of the mouse brain at various thicknesses are investigated to demonstrate the role of *Majorana* photons in potentially improving imaging with higher flux of photons in the classical limit. The radial and azimuthal beams are defined to be *Majorana*-like photons.

The brain is a biological tissue made up of neurons and axons in tree-like structure. Neurons are organized by integrated networks of proteins polymers, which are considered a chiral media. This chiral media will interact with the electromagnetic field of light by changing its state of polarization; this effect makes the brain a chiral bioplasma. Structured vector light is expected to interact with chiral matter by coupling with electric dipole, magnetic dipole and quadrupole moments and transitions from Fermi Golden Rule. The underlying unique and complex structure and properties makes the brain a "smart tissue"; due to this heterogeneity in the brain, different regions could show dissimilar effects. Electric quadrupole interactions enable the twisted light to twist more with a wavelength to be involved with local electronic transitions. Therefore, we decided to focus on main brain regions such as the cortex, white matter and hippocampus. White and grey (cortex and hippocampus) matter are considered major regions of the central nervous system. These are regions mainly affected by neurodegenerative diseases such as Alzheimer's and multiple sclerosis among others.

In the disclosed experiment, these brain regions are examined to determine whether there are special maze pathways in brain tissue for photons to propagate as radial and azimuthal *Majorana* LG vortex for J beams. The polarization and OAM value l are changed for each localized spatial region. The goals are to observe if there is a direct proportionality between the OAM l and the transmission, and chiroptical interactions between a targeted region in the brain and each polarization used. Chiroptical effects involve interplay of chirality of molecular and electromagnetic radiation to produce energy shifts to the handedness of circular polarized photons such as circular dichroism in solids, liquids and biofluids. Proteins possess chiral to be probed.

Prior studies have been done where mouse brain transmission with LG was also analyzed for linear polarized light with no classical entanglement. No transmission difference effect was observed for linear polarization (LP) on OAM (l). Here, the polarized states are further expanded to include classical entangled beams with circular, radial, and azimuthal polarization for OAM of LG beams for *Majorana*. One can expect that circular polarization and entangled light beams will affect the photons absorption rates. The use of classical entanglement is that it operates locally and uses a high flux of photons in contrast to quantum entanglement that uses a single low photon number non-locally.

*Majorana* and other states of polarization and spatial modes of photons: Vector beams are spatial modes with varying states of polarization. Radial polarized (RP) and azimuthal polarized (AP) modes can produce stronger longitudinal electric and magnetic field components upon focusing. RP can also generate smaller spot size upon focusing by a high NA objective lens to form imaging in nano scale. Most importantly, RP and AP are nonseparable beams (mixed states) in space and polarization, being classically entangled. These modes are defined and attributed as *Majorana* boson photons as shown to be $\psi=\psi^*$.

The following represents the four polarization states in Dirac notation and Jones vector. Equation (1) is a linear polarization, which is a state representation of right and left circular polarization.

$$|LP\rangle = |RH\rangle + |LH\rangle \qquad (1)$$

Equation (1) contains polarization spinning together in opposite directions as RH-CP and LH-CP.

Circular polarization can be written in a more general form as shown in Eq. (2) as a pure state:

$$|CP\rangle = \cos\phi|x\rangle \pm \sin\phi e^{i\delta}|y\rangle \qquad (2)$$

where $\phi$ represents the azimuthal phase at $\pi/4$ with respect to the x-axis and $\delta$, which is the complex phase taken at $\pi/2$, $|+\rangle$ and $|-\rangle$ are two general eigenvector states, which represent two column vectors $$\begin{pmatrix}1\\0\end{pmatrix} \text{ and } \begin{pmatrix}0\\1\end{pmatrix}.$$

Equation (3) represents right-handed circular polarization:

$$|RH\rangle = \frac{1}{\sqrt{2}}\begin{pmatrix}1\\-i\end{pmatrix} == \frac{1}{\sqrt{2}}[|+\rangle - i|-\rangle] \qquad (3)$$

Equation (4) represents left-handed circular polarization:

$$|LH\rangle = \frac{1}{\sqrt{2}}\begin{pmatrix}1\\i\end{pmatrix} == \frac{1}{\sqrt{2}}[|+\rangle - i|-\rangle] \qquad (4)$$

where $|RH\rangle^* = |LH\rangle$.

Laguerre-Gaussian beams with circular polarization (pure states) are represented by Eq. (5):

$$|\ell|RH\ell; |-\ell|RH\ell; \text{ and } |\ell|LH\rangle; |-\ell LH\ell \qquad (5)$$

where $\ell$ represents the OAM value.

Radial polarized beam shows the mixed of *Majorana*. Equation (6) shows radial polarization (classical entangled local state) with spatial and polarization:

$$|RP\rangle = \frac{1}{\sqrt{2}}\begin{pmatrix}\cos\phi\\\sin\phi\end{pmatrix} \rightarrow \frac{1}{\sqrt{2}}\left[e^{i\phi}\begin{pmatrix}1\\-i\end{pmatrix} + e^{-i\phi}\begin{pmatrix}1\\i\end{pmatrix}\right] == \frac{1}{\sqrt{2}}\left[e^{i\phi}|RH\rangle + e^{-i\phi}|LH\rangle\right] \qquad (6)$$

The notation in Eq. (6) shows that radial polarization is a superposition of two states |RH and |L. The exponent is a variation phase and is a unique characteristic of vortex beams. This one proves to be a *Majorana* photon. Laguerre-Gaussian beams with radial polarization are *Majorana* photons represented by Eq. (7), which is a mixed of states:

$$|LG_{RP}\rangle \frac{1}{\sqrt{2}}[|-\ell\rangle|LH\rangle + |\ell\rangle|RH\rangle] \qquad (7)$$

Equation (8) represents azimuthal polarization (classical entangled local mixed state) with spatial and polarization as another *Majorana* photon:

$$|AP\rangle = \frac{1}{\sqrt{2}}\begin{pmatrix}-\sin\phi\\\cos\phi\end{pmatrix} \rightarrow \frac{1}{\sqrt{2}}\left[e^{i(\phi+\pi/2)}\begin{pmatrix}1\\-i\end{pmatrix} + e^{-i(\phi+\pi/2)}\begin{pmatrix}1\\i\end{pmatrix}\right] == \qquad (8)$$
$$\frac{1}{\sqrt{2}}\left[e^{i(\phi+\pi/2)}|RH\rangle + e^{-i(\phi+\pi/2)}|LH\rangle\right]$$

The notation in Eq. (8) shows that azimuthal polarization is also made of a superposition of $|RH\rangle$ and $|LH\rangle$. However, the variation phase has an extra $\pi/2$ phase shift.

*Majorana* Laguerre-Gaussian beams with azimuthal polarization are represented by Eq. (9), which is a mixed of states:

$$|LG_{AP}\rangle \frac{-i}{\sqrt{2}}[|-\ell\rangle|LH\rangle - |\ell\rangle|RH\rangle] \qquad (9)$$

Taking the complex conjugate of Eq. (3) and (4) of pure circularly polarized states give the following equations:

$$|RH\rangle^* = |LH\rangle \qquad (10)$$

$$|LH\rangle^* = |RH\rangle \qquad (11)$$

which shows that Eq. (10) and Eq. (11) are not *Majorana*. However, taking the complex conjugate of a linear polarization Eq. (1), proves to be a *Majorana* photon as shown in Eq. (12):

$$|LP\rangle^* = \frac{1}{\sqrt{2}}\left(\begin{pmatrix}1\\i\end{pmatrix} + \begin{pmatrix}1\\-i\end{pmatrix}\right) = |LH\rangle = \frac{1}{\sqrt{2}}\left(\begin{pmatrix}1\\-i\end{pmatrix} + \begin{pmatrix}1\\i\end{pmatrix}\right) \qquad (12)$$

Moreover, taking the complex conjugate of vector beams (radial and azimuthal) from Eqs (13) and (14), shown below:

$$|RP\rangle^* = |RP\rangle \qquad (13)$$

$$|AP\rangle^* = |AP\rangle \qquad (14)$$

proves that Eq. (13) and Eq. (14) follow the *Majorana* feature of $\psi=\psi^*$, being Hermitian as shown in Eq. (15).

$$C = a + a^\dagger = C^* \qquad (15)$$

where a and a-dagger $a^\dagger$ represent the creation and annihilation operators of a *Majorana* photon.

Quantum field theory can be describe the electric field E and Vector field $A=\psi$ operators from a and $a^\dagger$ using the polarization.

In addition, radial and azimuthal photons are *Majorana* quasi photon particles for propagating in biological and condensed scattering media.

The photon can excite electrons causing vibrations, which couple to the media quasi-particles to become a coupled quasi-particle or a polariton depending on how w gets close to the resonance frequency $\omega_o$. These quasi-particles commonly become one of the following: optical phonon, exciton, plasmon, and/or magnon-polariton. The dielectric media can be represented by. It is known that photons can couple to plasmons, optical photons, magnons and excitons. The photon excitations became a quasi particle from the interactions and become dressed. Quasi particles can be made up of three sub entities: Holons (charge), Orbitons, and Spinons. A *Majorana* photon quasi-particle can be split into spin and orbital in OAM and SAM optical beams.

Special paths may exist in the brain for photons to travel through. The brain is very different from other body organs such as the breast, cervix, skin and kidney. It has special tree-like structure with connections of 86 billion neurons and axon branches to store and retrieve information from memory. There are 6 different types of nerve cells in the central nervous system, which are nourished and protected by neuroglia or glial cells (glue like media). The photons enter the brain and travel in this maze, interacting with existing chiral proteins and lipid molecules. There is a possible existence of optical waveguide fiber-like lanes in the brain from microtubules that the photon may take upon exiting. If these classical non-separable structure modes exist in the chiral brain, they would increase the transmission and retain coherence. These special photon quasi-particles can be more transmitted and retain the input characteristics and be entangled with sister photons. We have introduced a new *Majorana* quasi-particle photon that differs from pure states of CP in the brain.

Material and Methods

Figure 2:
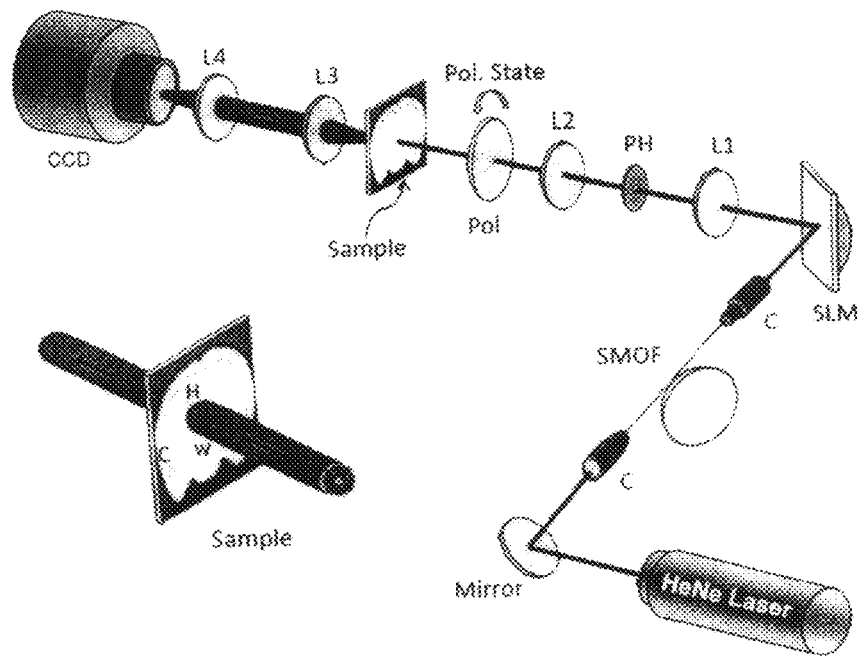
FIG. 2 shows the general experimental setup. M, mirror; C, collimator; SMOF, single mode optical fiber; SLM, spatial light modulator; L, lenses; PH, pinhole; Pol. State, four different types of polarization; S, sample; CCD, charge coupled device camera. Sample parts: A—hippocampus; B— white matter; C— cortex.

FIG. 2 shows the experimental setup where a He—Ne laser of 5 mW at 633 nm (horizontally polarized) was used as a light source, focusing onto a single-mode optical fiber (SMOF). The output beam from the optical fiber passed through a collimator and illuminated the spatial light modulator (SLM), which was set at reflection mode. The SLM produced LG beams of different $\ell$ values that were generated by different forked diffraction patterns. A first lens was used to collimate the first order diffraction through a 400-µm aperture, decreasing the beam's overall exposure to light. A second lens was then used to recollimated the beam. Then the LG beam with specific polarization (see next paragraph) went through a healthy mouse brain sample. Finally, the beam went through a 4f imaging system constituting of two lenses (L3=5 cm, L4=10 cm). A CCD camera detected the output.

To generate the *Majorana* vector beams with various OAM values, we combined a spatial light modulator (SLM) with a vortex retarder (VR). A SLM is a phase and amplitude modulator that generates vortex beams by inputting computer generated holograms onto the phase of the SLM. A vortex retarder (VR) is a spatially inhomogeneous phase retarder. The one used in the experiment is a $\ell=1$ vortex retarder, which is polarization dependent. In the experiment (FIG. 2), the SLM will generate a vortex beam with $\ell$ value, which will be combined with the VR $\ell$ value, creating a vortex beam with a total value of OAM. In order to generate the *Majorana* vector beams with a specific polarization, we fixed the fast axis of the VR to one direction. Then, we sent in different orientation of linear polarization with respect to the axis of the VR. To generate a radially polarized beam, a horizontally polarized beam has to go through a vortex retarder (VR) with respect to its optical axis. To generate an azimuthally polarized beam, a vertically polarized (horizontally polarized beam going into a half wave plate) beam needs to go through the VR with respect to its optical axis. Finally, to generate scalar vortex beams we only used the SLM set at different $\ell$ values. To generate the circularly polarized light, a linear polarized beam needs to pass through a quarter wave plate at an angle of 45°. Also a half wave plate can be used to generate a left circularly polarized beam.

Brain Tissue Preparation: The brain tissue samples were prepared following the procedures approved by the Institutional Animal Care and Use Committee (IACUC) of the City College of New York under Adrian Contreras. A wild type adult mouse was anesthetized with isoflurane. After the mouse was completely anesthetized (confirmed with no response upon toe pinch), it was decapitated, and the brain was dissected and fixed in 4% paraformaldehyde overnight. The fixed brain was processed with coronal section by using a compresstome (VF300, Precision Instruments, Greenville, N.C.) at two different thicknesses (120 and 600 respectively). The accuracy in tissue slice thickness was ±1 µm.

Data collection and analysis: Data was collected for a 120 µm and a 600 µm thick brain tissues for linearly, circularly, radially, and azimuthally polarized beams at different positive $\ell$ values ($\ell=0, 1, 3, 5, 7$), respectively. Also, the size of the OAM beam for each $\ell$ value was taken into account when sending it through each region of the brain sample. In the 120 thick tissue, the LG beam penetrated the cortex, the hippocampus, and white matter. The propagation of the LG beam is considered to be ballistic as the thickness of the sample results in a lack of scattering and interference in the trajectory of the LG beam, creating a straight path of travel 41. In the 600 µm tissue, the LG beam penetrated the cortex and white matter (FIG. 1). The propagation of the LG beam is considered to be diffusive as the increased thickness of the sample results in greater scattering of the LG beam. Furthermore, a reference beam was also measured with no sample to take into account the change of incident light in calculating the transmittance. Finally, the data was analyzed using ImageJ software and by equation (16) as shown below:

$$\text{Transmitted intensity} = \frac{Ts}{Tns} = 10^{-OD} \tag{16}$$

where $T_s$ is transmitted intensity with sample, $T_{ns}$ is the transmitted intensity with no sample.

Results and Discussion

Figure 3:
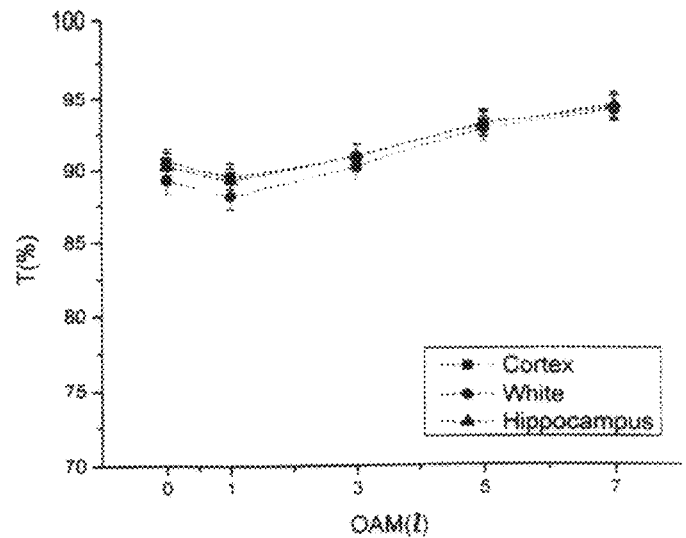
FIG. 3 shows a graph of transmittance (T) through a 120-μm sample as a function of OAM (l) for a collimated horizontally polarized LG beam.

The data in FIG. 3 shows transmission difference between the cortex, white matter and hippocampus for a horizontally polarized collimated LG beam as a function of OAM with the tissue thickness of 120 µm. As shown below the transmittance after $\ell=1$ in all targeted areas increases proportionately with $\ell$ However, this increase is very small as the transmission ranged is about 6%.

Figure 4:
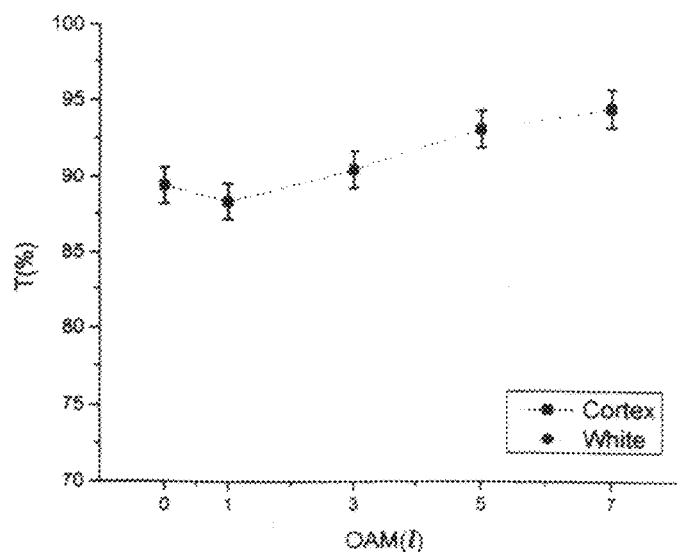
FIG. 4 is a graph of transmittance (T) through a 600-μm sample as a function of OAM (l) for a collimated horizontally polarized LG beam.

FIG. 4 shows transmission difference between the cortex and white matter for a horizontally polarized collimated LG beam as a function of OAM with the tissue thickness of 600 In this case, the transmission range is also about 6%. These results further verify that the relationship between $\ell$ and transmittance of linearly polarized light through brain tissue is almost insignificant. In addition, this is theoretically proved by Forbes and Andrews that linearly polarization will have little to none chiroptical response from only OAM unlike circular polarization.

Figure 5:
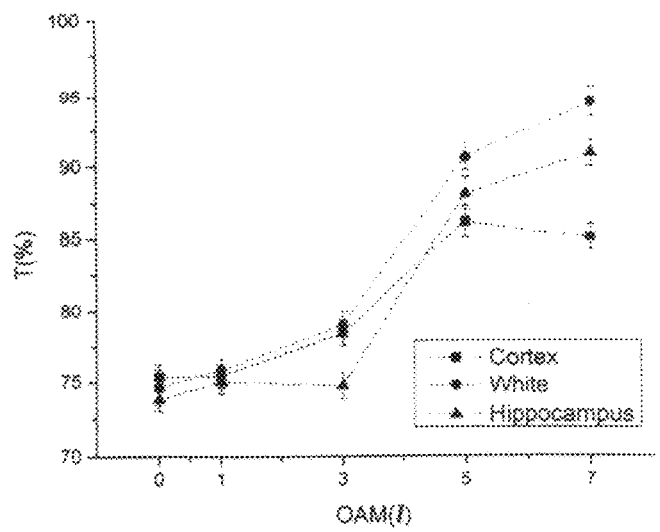
FIG. 5 is a graph of transmittance (T) through a 120-μm sample as a function of OAM (l) for a collimated left circularly polarized LG beam.

FIG. 5 shows transmission difference between the cortex, white matter and hippocampus for a left circularly polarized collimated LG beam as a function of OAM with the tissue thickness of 120 The transmittance of the beam generally increases as $\ell$ increases in all targeted parts. The sharpest increase in transmittance can be seen from $\ell=3$ and above, in which all of the transmittance graphs share a similar curvature. Targeting the white matter consistently yields the highest transmittance, whereas targeting the hippocampus yields the lowest transmittance from $\ell=0$ to slightly before $\ell=5$, and targeting the cortex yields the lowest transmittance from slightly greater than $\ell=5$ onward. The overall transmission range achieved is about 20%.

Figure 6:
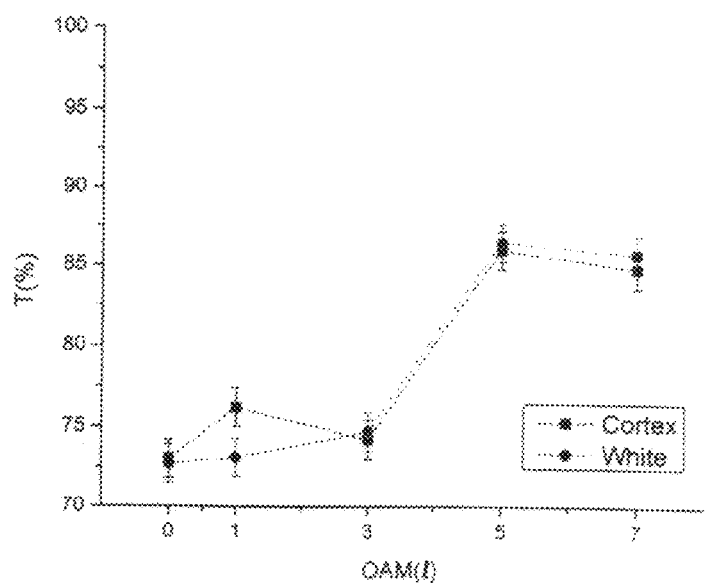
FIG. 6 is a graph of transmittance (T) through a 600-μm sample as a function of OAM (l) for a collimated left circularly polarized LG beam.

FIG. 6 shows transmission difference between the cortex and white mater for a circularly polarized collimated LG beam as a function of OAM with the tissue thickness of 600 µm. FIG. 5 displays a similar, yet slightly weaker trend between $\ell$ and transmittance, as the graphs in FIG. 5 and FIG. 6 share similar curvatures and both display that a slightly higher amount of transmittance is achieved when targeting white matter versus targeting the cortex (specifically from $\ell=3$ to $\ell=7$). The overall transmission range achieved is about 14%. In addition, left circular polarization shows a high transmission variation. This could be expected due to the interaction of the handedness of beam and the different values of the OAM, and due to its pure state nature.

Figure 7:
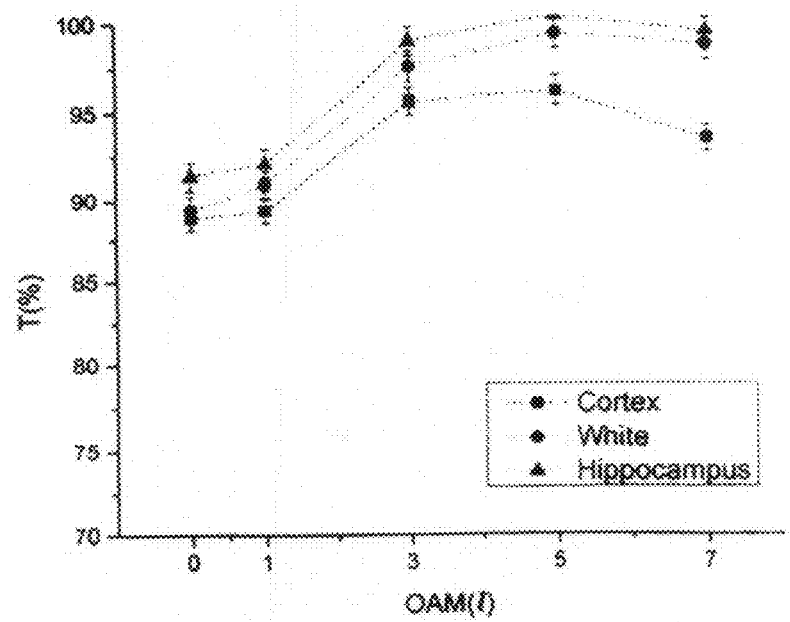
FIG. 7 is a graph showing *Majorana* transmittance (T) through a 120-μm sample as a function of OAM (l) for a collimated radially polarized LG beam.

The transmission in FIG. 7 shows difference between the cortex, white matter and hippocampus for a radially polarized collimated *Majorana* LG beam as a function of OAM with the tissue thickness of 120 The transmittance of the LG beam consistently increases as $\ell$ increases in all targeted regions and begins to wane as $\ell$ approaches 7. The sharpest increase is experienced from $\ell=0$ to $\ell=3$. Targeting the hippocampus consistently yields the highest transmittance while targeting the cortex consistently yields the lowest transmittance. The overall transmission range achieved is about 12%.

Figure 8:
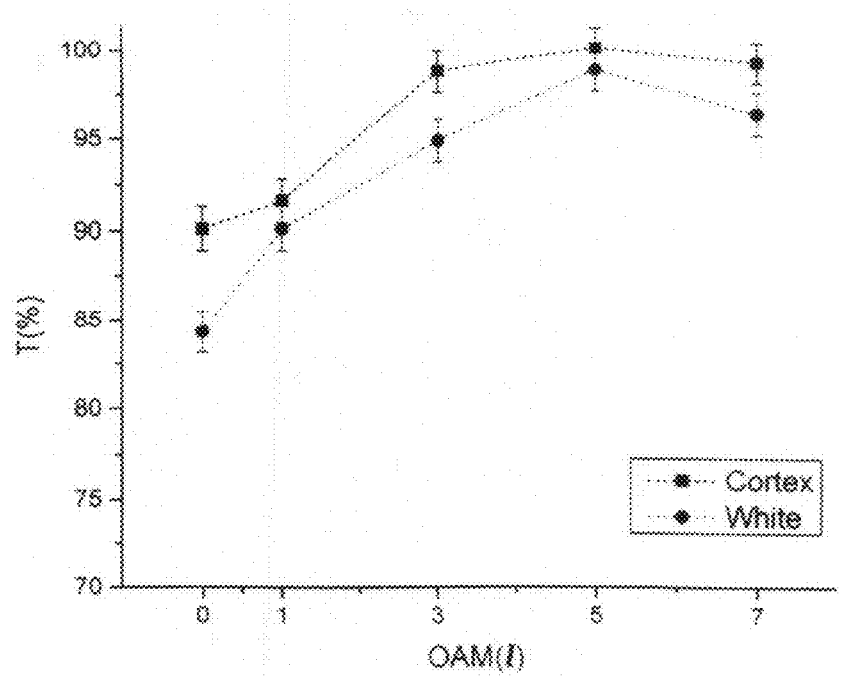
FIG. 8 is a graph showing *Majorana* transmittance (T) through a 600-μm sample as a function of OAM (l) for a collimated radially polarized LG beam.

FIG. 8 shows transmission difference between the cortex and white matter for a radially polarized collimated LG beam as a function of OAM with the tissue thickness of 600 μm. It shows a similar positive relationship between $\ell$ and the transmittance. Also the cortex shows a greater transmission than white matter. The overall transmission range achieved is about 16%.

Moreover, radial polarization shows a high transmission range and well defined trend for each of the targeted regions. This is also expected due to the fact that radial is a superposition of left and right circular polarization.

Figure 9:
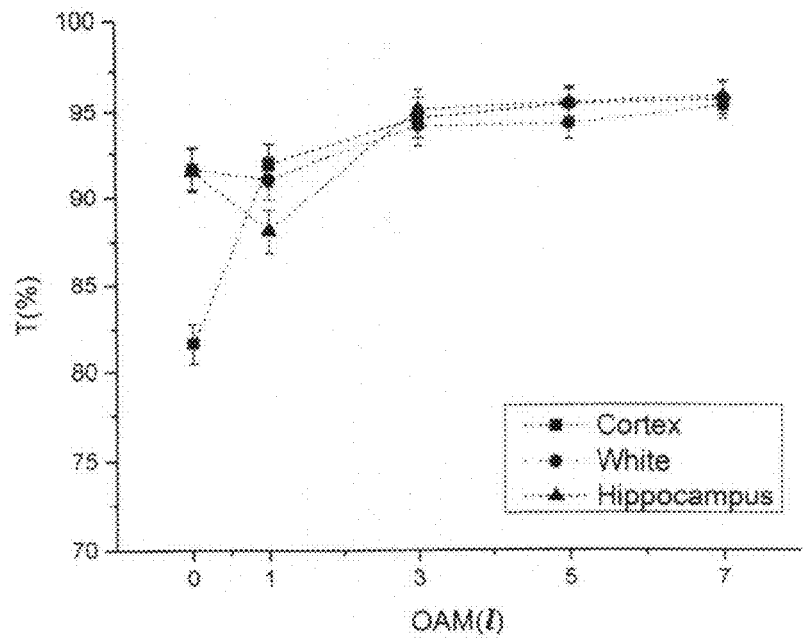
FIG. 9 is a graph showing *Majorana* transmittance (T) through a 120-μm sample as a function of OAM (l) for a collimated azimuthally polarized LG beam.

FIG. 9 shows transmission difference between the cortex, white matter and hippocampus for azimuthally polarized collimated LG beam as a function of OAM with the tissue thickness of 120 The transmittance of the beam increases from $\ell=1$ to $\ell=7$. One difference that can be seen in all three regions is that from $\ell=0$ to $\ell=1$, only the transmittance for the cortex increases, while the transmittance for the white matter and hippocampus decreases. The overall transmission range achieved is about 14%.

Figure 10:
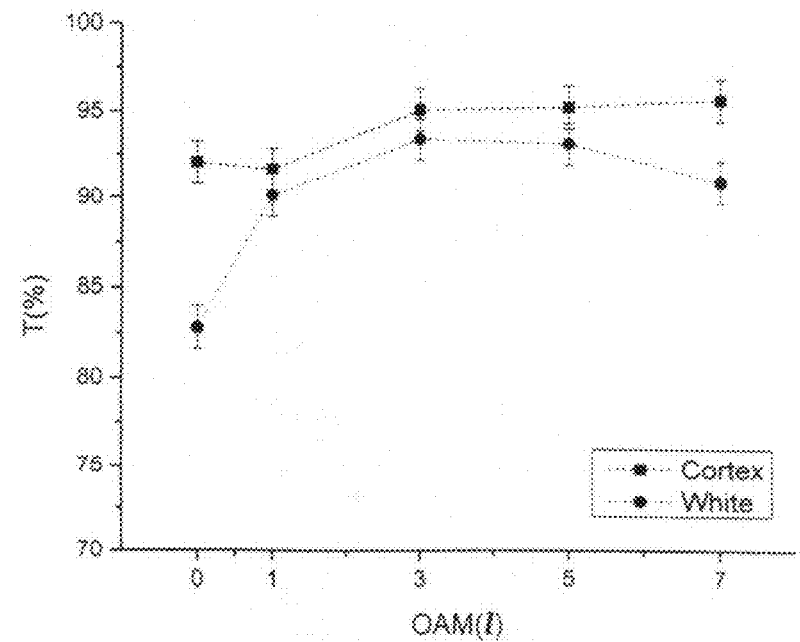
FIG. 10 is a graph showing *Majorana* transmittance (T) through a 600-μm sample as a function of OAM (l) for a collimated azimuthally polarized LG beam.

FIG. 10 shows transmission difference between the cortex and white matter for azimuthally polarized collimated LG beam as a function of OAM with the tissue thickness of 600 μm. This figure shows a constantly higher transmission for cortex with respect to the $\ell$ values. In the case of white matter, the transmittance only increases from $\ell=0$ to $\ell=3$, after that the transmittance goes down. The overall transmission range achieved is about 13%. Additionally, azimuthal polarization shows a high overall transmission. Just like in the radial polarization case, this is also expected for azimuthal, being that is also made of left and right circular polarization.

The vortex beam produced the salient outcome that the transmittance of LG beams through brain tissue displays strong positive dependency on OAM for collimated, radially, azimuthally and left circularly polarized LG beams.

The *Majorana* beams of radial, azimuthal and linear polarization gave the highest transmission and less variation with OAM. However, the left circular polarization showed a large variation as the $\ell$ values increase due to the fact of being a pure circular polarization state. The vector beams showed less variation with the $\ell$ values, this is due to their non-separability and dual chirality nature. Moreover, vector beams gave clear trends when targeting different areas of the brain at the ballistic and diffusive region. Radial polarization gave the highest transmission range at the diffusive region, while left circular polarization showed the highest transmission for the ballistic region. Moreover, in targeting the hippocampus, cortex, and white matter, radially polarized light proved to be the most effective. Hence, these results support the idea that light transmission through different areas of the brain varies.

Moreover, these results allow for the optimization of optical brain imaging depending on which brain region is being targeted. For example, by targeting specific regions affected by neurodegenerative diseases, we are able to understand and learn more about the mystery behind these diseases with the aim of preventing or treating it. Also, the use of this imaging method at different brain regions will differentiate an abnormal brain tissue from a normal one. For a future project we plan to do brain transmission and imaging on a human brain with Alzheimer's disease, focusing on areas that are mainly affected such as hippocampus, cingulate gyms, and amygdala. In addition, Forbes and Andrews showed dipole and quadrupole have a chiroptical effect associated with OAM with circular dichroism (left and right circular polarization). Afanasev and colleagues have shown that higher multipole transitions exhibit circular dichroism with OAM ($\ell$) dependency, in non-chiral atomic matter.

In conclusion, the radial and azimuthal, which are non-separately mixed photon states, and linear polarized beams are shown to be *Majorana* photons, shown in lKet>Dirac notations. A *Majorana* photon has within itself both direction of time and right and left handed twists; recapping that the photon and antiphoton are identical 1. These special entangled *Majorana* photon modes may be at the heart of the future optical and quantum computers as *Majorana* quasi photon qubits store and transfer information with less scattering and interference from the environment.

The disclosed system finds applications in two-photon fluorescence (TPF) imaging, second harmonic generation (SHG) imaging, third harmonic generation (THG) imaging and nonlinear optical (NLO) imaging. Imaging depth can be, for example, 1 μm to 1000 μm or, in other embodiments, multiple centimeters in depth. The wavelength of light may be, for example, a wavelength between 650 nm to 950 nm (NIR window), 1000 nm to 2500 nm (SWIR window) or 1600 to 1870 nm (golden window).

New types *Majorana*-like photons are presented, which are attributed to both polarization and wavefront of special function class of optical vector vortex beams [1,2]. A *Majorana* photon is a photon that is identical to its antiphoton [3,4]. It has within itself both chirality, right and left-handed twist in polarization and wavefront. These spin-orbit coupled beams includes radial, and azimuthal of optical functions such as Laguerre-Gaussian, hybrid π-vector beams, and Airy beams [1].

The polarized basis modes in Eqs. (1) and (2) show the salient feature of a Laguerre-Gaussian beam with radial and azimuthal polarization (non-separable states) with spatial wavefront and polarization by using the wave Dirac Ket notation function:

$$|\psi_{RP_{LG}}\rangle = \frac{1}{\sqrt{2}}[e^{i\ell\varphi}|RH\rangle + e^{-i\ell\varphi}|LH\rangle], \quad (17)$$

$$|\psi_{AP_{LG}}\rangle = \frac{i}{\sqrt{2}}[e^{i\ell\varphi}|RH\rangle - e^{-i\ell\varphi}|LH\rangle]. \quad (18)$$

Both vector beams (Eq. 17 and Eq. 18) show to be on a superposition of two orthogonally components, |RH⟩ and |LH⟩ circularly polarized states of $\pm\ell$. These two equations are also known as cylindrical transverse modes or higher-order transverse modes, which can be geometrically represented by using a higher-order Poincaré sphere (HOPS).

Equation 17 is an analog representation of the transverse electric mode ($TE_{01}$), while Equation 18 is an analog representation of the transverse magnetic mode ($TM_{01}$). These types of modes occur in optical fibers and in optical resonators.

In addition, other types of fiber waveguide modes are the hybrid modes ($HE_{21}$) known as π-vector beams, which have non-zero electric and magnetic fields in the direction of propagation. They are also represented through HOPS, which describes various polarizations of optical fiber waveguides. These hybrid-polarized modes are mathematically represented through Equation 19 and Equation 20 as OAM modes:

$$|HE\rangle_{even} = \frac{1}{\sqrt{2}}\left[e^{-i\ell\varphi}|RH\rangle + e^{i\ell\varphi}|LH\rangle\right] \quad (19)$$

$$|HE\rangle_{odd} = \frac{i}{\sqrt{2}}\left[-e^{-i\ell\varphi}|RH\rangle + e^{i\ell\varphi}|LH\rangle\right] \quad (20)$$

Therefore, vector beams (radial and azimuthal) and hybrid π-vector beams from Equations 17 through 20, are defined and attributed as *Majorana*-like photons from the basis modes, following the *Majorana* feature of $\psi=\psi^*$ as shown below in Equation 21 and Equation $$\left(\psi_{RP_{LC}}\right)^* = |\psi_{RP_{LG}}\rangle; \left(\psi_{AP_{LG}}\right)^* = |\psi_{AP_{LG}}\rangle, \quad (21)$$

$$|HE\rangle^*_{even} = |HE\rangle_{even}; |HE\rangle^*_{odd} = |HE\rangle_{odd} \quad (22)$$

Other spatially structured light beams such as Airy beams (AiB) follow the *Majorana* fingerprint of $\psi=\psi^*$, base modes where the photon and the anti-photon are identical. This type of complex beams is also a solution to the paraxial Helmholtz wave equation expressed in different coordinate systems. Besides, this beam has a special property of non-diffracting and self-healing when propagating through an obstruction.

Equations 23 and 24 represent vector Airy beams written in terms of Jones vector of RCP and LCP, a helical phase front of $e^{i2q\varphi}$, and with the characteristic Airy cubic phase modulation of $\exp(i(x^3+y^3))$, where q is half of the topological charge $\ell$, and θ is the angle between the incident polarization direction and the x-axis $$|\psi_{RP_{AiB}}\rangle = \frac{1}{\sqrt{2}}\left[e^{i\ell\varphi}e^{i(x^3+y^3)}e^{-i\theta}|RH\rangle + e^{-i\ell\varphi}e^{-i(x^3+y^3)}e^{i\theta}|LH\rangle\right], \quad (23)$$

$$|\psi_{AP_{AiB}}\rangle = \frac{i}{\sqrt{2}}\left[e^{i\ell\varphi}e^{i(x^3+y^3)}e^{-i\theta}|RH\rangle - e^{-i\ell\varphi}e^{-i(x^3+y^3)}e^{i\theta}|LH\rangle\right]. \quad (24)$$

Taking the complex conjugate of Equation 23 and 24, proves that indeed these types of vector vortex polarization beams are *Majorana*-like photons as shown below in Equation 25 and 26:

$$\left(\psi_{RP_{AiB}}\right)^* = \quad (25)$$
$$\frac{1}{\sqrt{2}}\left[e^{-i\ell\varphi}e^{-i(x^3+y^3)}e^{i\theta}|LH\rangle + e^{i\ell\varphi}e^{i(x^3+y^3)}e^{-i\theta}|RH\rangle\right] = |\psi_{RP_{AB}}\rangle,$$

$$\left(\psi_{AP_{AiB}}\right)^* = \quad (26)$$
$$\frac{-i}{\sqrt{2}}\left[e^{-i\ell\varphi}e^{-i(x^3+y^3)}e^{i\theta}|LH\rangle - e^{i\ell\varphi}e^{i(x^3+y^3)}e^{-i\theta}|RH\rangle\right] = |\psi_{AP_{AB}}\rangle.$$

In quantum field theory (QFT), the second quantization formalism in terms of the harmonic creation ($a^\dagger$) and annihilation (a) operators is useful for the analysis and characterization of the quantum optics properties and can be used to describe features of the *Majorana* vector photons. The *Majorana* boson creation ($b^\dagger$) and annihilation (b) operators can be written in terms of harmonic operators ($a^\dagger$) and (a), where $b^\dagger=(a^\dagger+a)/\sqrt{2}$ and $b=(a+a^\dagger)/\sqrt{2}$.

Using the *Majorana* boson creation ($b^\dagger$) and annihilation (b) operators, the *Majorana* boson operator can be represented as follows (Eq. 27):

$$C=b+b^\dagger=C^\dagger, \quad (27)$$

where the wave function of the quantum field is its anti-conjugate.

*Majorana*-like photons arise from radial and azimuthal Laguerre-Gaussian, Airy beams, and hybrid π-vector beams. These belong to a super class of special functions and are characterized as cylindrical polarized transverse and hybrid vector vortex photons. These special vector beams are known as eigenmodes of weakly guiding optical fibers. They have identical anti-conjugate state and complex transpose ($\psi=\psi^*$) in its polarization field and wavefront.

Figure 11:
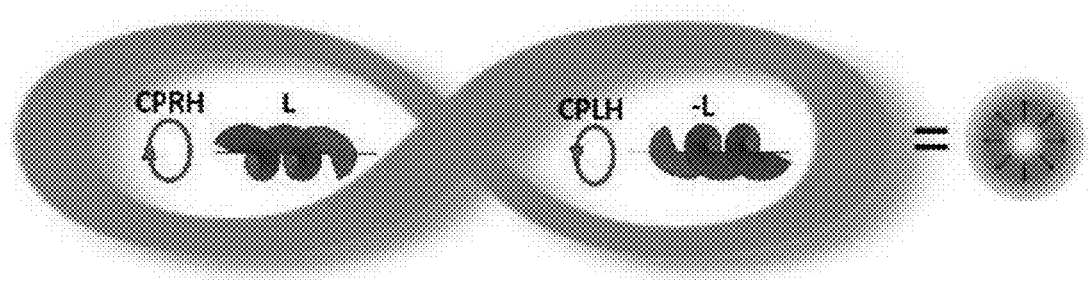
FIG. 11 shows a *Majorana* photon, which is a mixture of SAM and OAM coupled together, where the *Majorana* is Radially polarized twisted photon.

FIG. 11 shows a *Majorana* photon, which is a mixture of SAM and OAM coupled together. In this case it is a *Majorana*-Radially polarized twisted photon.

It is well known that Fractal dimension D can be described by any possible real number such as whole numbers from 1, 2, and 3 or a fraction like D=1.25, 1,5 etc. to describe their complexity and repeating object structure like snow flakes, tree branches, maps of country, clouds among others.

One can generate fractal patterns of wave front from laser mode patterns. Complex wave front pattern from CVV can be produce using Vortex plates or Spatial Light Modulators. We teach here using different colors of light of lasers and various colors in Supercontinuum (SC) in laser beam (FIG. 12) to have a pattern of dimension D SC(λ) and upon passing a media—brain, breast, tissue, cells, fog—the dimension D change to D' SC for different wavelengths λ, the difference in D can be used as diagnostic parameter: Δ D (λ)=D−D'.

Figure 12:
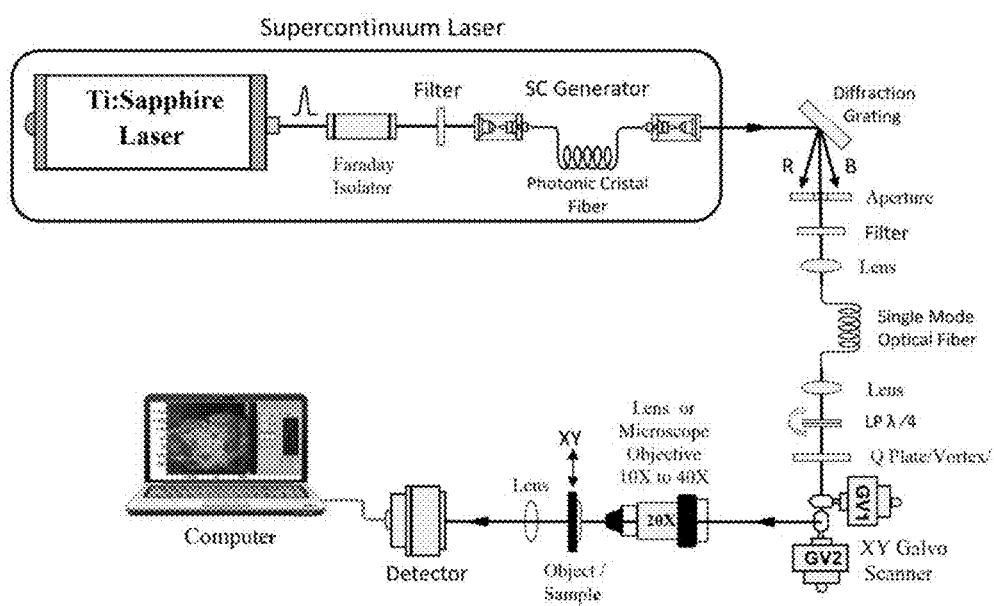
FIG. 12 shows the design for SC microscope with and without *Majorana* or CVV OAM.

FIG. 12 shows the design for SC microscope with and without *Majorana* or CVV OAM for various applications such as for a Light scattering to get size of micro and nano particles and imaging from various wavelengths in supercontinuum from UV to NIR. This SC system consist of ultrafast laser, dielectric media or fiber to generate SC source, grating or filters to separate wavelengths and array of optics, lens, spiral plate, phase plate, polarizers, half and full wave plates, and galvo scanner to get 2D images and display angles. Some of these elements are need to produce CVV, OAM and *Majorana* beams of different L=0, 1, 2, 3, . . .

Light-matter interaction of Fractal *Majorana* light. The use of fractal structure at various dimensions for application in imaging. This type of light can carry complex shapes along with polarization (*Majorana* and non-*Majorana*) and OAM values and be used to study the complexity of the brain or tissue diagnosis (cancer vs normal), enhancing special features of these biological tissues.

The use of Supercontinuum with and without *Majorana* beams and other CVV beams with various fractal structures for the use of light scattering study of biological tissues (brain, breast, etc.). This is done by sending SC laser beam with various patterns of dimension D SC(λ) and upon passing a media—brain, breast, tissue, cells, fog—the dimension D change to D' SC for different wavelengths λ, the difference in D can be used as diagnostic parameter: A D (λ)=D−D'.

The use of the SC-*Majorana* CVV system and SC beam to detect and determine the size of small particles size 'a' of size um and nano, using different wavelengths from SC in angle dependence and from ratio of Forward and Backward scatterings intensity.

Use of UV light 100 nm to 250 nm to measure nano particles from 50 nm to 500 nm from ratio of BS to FS and from angle of scatter θ=λ/a where "a" is the size of a particle (such as virus or bacteria) and λ is the wavelength.

Use of light 300 nm to 2500 nm to measure nano particles from 1 um to 1000 um from ratio of BS to FS and from angle of scatter θ=λ/a where "a" is the size of a particle (such as virus or bacteria) and λ is the wavelength.

Using the angular dependence of light scattering from small particles such as micron size for example for pollen, water drops, etc.; and nanometer size virus (100 nm to 200 nm) using SC, UV lamp, LED, using the scattering angle equation θ=λ/a. Each one depends on the wavelength (λ) from particle "a" from um to nm size from UV to NIR. Example: SC Red scatters at λ more than Blue.

Using a lens in detection present and size of small particle where you place a Len of focal length f away from CCD camera/Video to get position (Tan θ=r/f) of the scattered light. Using Both relation one can find the size of particle "a" from: θ=r/f=λ/a by measuring r on CCD via software.

The use of SC-*Majorana* Microscope for edge enhancement for biomedical samples such as cells and tissues to obtained detailed features. This system can also be helpful to detect disease such as cancer or tumors.

The use SC-*Majorana* system can also be applied as a hybrid mode-wavelength division multiplexer. This is achieved by exploring various wavelengths coming from SC and also the various polarizations coming from a q-plate, along the OAM modes carried by each polarization topology. This system can improve link capacity in wireless networks. The use of a q-plate in the system can make the achievement simpler because a q-plate is a tunable device controlled by external voltage, acting as a switcher.

In view of the foregoing, *Majorana* photons, in its various iterations, have numerous applications.

Accordingly, a method for imaging a biological tissue sample includes the steps of: transmitting *Majorana* photons through the biological tissue sample, wherein the *Majorana* photons are a mixed state of spin angular momentum (SAM) and orbital angular momentum (OAM) (chiral entangled state), such beams having radial polarization an azimuthal polarization, thereby producing transmitted *Majorana* photons; receiving the transmitted *Majorana* photons with an optical receiver, thereby producing a received signal; and processing the received signal to produce a digital image of the biological tissue sample, a brain tissue sample, for example.

The *Majorana* beams can be used with application on multiphoton imaging using higher resolution, obtained from a focused vector beam (small spot size) using a high numerical aperture (NA).

*Majorana* and non-*Majorana* beams can be used to provide deep imaging. As shown, *Majorana* vector beams have a deeper penetration (almost near >90% transparency) into bio-media, such as brain and breast tissue. Also, transmission of a non-*Majorana* such as circularly polarized beams has a greater dependency on OAM. Imaging depth can be, for example, 1 μm to 1000 μm or, in other embodiments, multiple centimeters in depth. The method has applications to Window III (1600-1870 nm) NIR optical brain tissue, known as the golden window in the brain. This region is known as being best for deeper brain imaging because of reduction in scattering and minimal absorption.

Imaging lipids and collagen in window III by linear photon imaging with *Majorana* can be used for deeper imaging for cancer and diseases.

*Majorana* beam also has applications in two-photon fluorescence (TPF) imaging, second harmonic generation (SHG) imaging, third harmonic generation (THG) imaging and enhancing nonlinear optical (NLO) imaging.

*Majorana* vector vortex beams in optical quantum computing are more likely to have a topological effect due to their various types of properties such as non-separability or non diffracting or self-healing. This is also based on the fact that *Majorana* vector beams are basis states of information.

*Majorana* vector vortex beams can also be used in topological quantum computing.

*Majorana*-photons can form knots and braids, which are similar to the DNA structure mode, providing a robust representation of the braid group, which is related to knot theory. Also, these *Majorana* photons are composed of natural braiding operators. In general, the inhomogeneous polarization and spin-orbit coupling characteristics of a vector beam could be an advantage when forming braids in 3D space, which represent logic gates in a computer. This type of optical quantum computer-based on knots and braids are more likely to conserve stability because a perturbation such as environmental will not change the topology of these beams, retaining input characteristics.

*Majorana* vector vortex beams can be used as a qubit-basic unit of quantum information.

*Majorana* photons are known for being intrinsically immune to de-coherence. Also, through vector beam modulation, it is possible to obtain N=4 possible states per pulse simultaneously which helps to encode log $N_2$=2 bits of information per ℓ value, rather than 1 bit of information with N=1 possible states as it happens with scalar beams.

*Majorana* vector beams can be used in imaging to improve imaging with a higher flux of photons in the classical limit. This is in contrast to quantum entanglement, which uses a single low photon number non-locally.

*Majorana* vector beams can also be used in transmission and imaging in bio-media or turbid media such as polystyrene beads. In previous experiment, *Majorana* beams showed improved deep penetration in mouse brain tissue. This could also be applied to other types of turbid and chiral media.

*Majorana* vector beams can also be used in quantum and optical communication. *Majorana* photons can help to increase transmission, transfer, and store more information with less scattering and possibly with less environmental interference (turbulence effect), maintaining the quantum coherence or just creating small perturbation.

*Majorana* vector beams also has application in high-resolution multiphoton microscopies (SRS, 2/3 PEF, SHG among others) due to the stronger longitudinal field obtained when a *Majorana*-radially polarized light is focused through a high numerical aperture (NA).

The samples are biological objects such as brain and breast tissue to improve the penetration depth and spatial resolution of the target, similarly to a dark field microscopy.

*Majorana* vector beams can be used in solid state and condensed matter physics. *Majorana* beams can help to unravel hidden optical transitions in a condensed matter such as in photoexcited-oriented carriers in semiconductors such as GaAs in conduction bands. This is also applicable in spintronics, since *Majorana* beams carry an entangled state of SAM and OAM, this may be used efficiently to transfer momentum to the spin polarized electrons in GaAs.

*Majorana* vector beams can be used in various fields of non-linear optics. *Majorana* beams have been proved to increased critical power requirement reducing nonlinear effects and

*Majorana*-like LG beams proved to be more resilient to multi-filamentation which demonstrates a resistance to beam profile break-up.

*Majorana* vector beams can be used in optical fibers. *Majorana*-like photons can attempt to limit challenges that fiber face such as scattering, attenuation, dispersion, nonlinear effects, and decoherence when traveling long distances.

The characteristics of these beams such as inhomogeneity spin-orbit coupling and topological invariant can be an advantage when propagating through long distance fibers. Meaning its property remains almost the same regardless of the scattering. In addition, *Majorana*-like beams will be less affected when fibers splice and the transmission losses will be less significant. Also, these *Majorana*-like beams have shown to decrease nonlinear effects and limit multi filamentation.

SC-*Majorana* CVV system and SC beams can be used to detect and determine the size of small particles size 'a' of size μm and nano, using different wavelengths from SC in angle dependence and from ratio of Forward and Backward scatterings intensity.

UV light of 100 nm to 250 nm can be used to measure nano particles from 50 nm to 500 nm from ratio of BS to FS and from angle of scatter $\theta=\lambda/a$ where "a" $\lambda$ is size of particle (such as virus or bacteria. Use of light 300 nm to 2500 nm to measure nano particles from 1 μm to 1000 μm from ratio of BS to FS and from angle of scatter $\theta=\lambda/a$ where "a" $\lambda$ is size of particle (such as virus or bacteria.

The angular dependence of light scattering from small particles such as micron size, for example for pollen, water drops, etc. and nanometer size virus (100 nm to 200 nm) using SC, UV lamp, LED, using the scattering angle equation $\theta=\lambda/a$. Each one depends on the wavelength ($\lambda$) from particle "a" from um to nm size from UV to NIR. Example: SC Red scatters at $\lambda$ more than Blue.

A lens can be used in detection presence and size of small particle where you place a Lens of focal length f away from CCD camera/Video to get position (Tan $\theta=r/f$) of the scattered light. Using both relations one can find the size of particle "a" from: $\theta=r/f=\lambda/a$ by measuring r on CCD via software.

SC-*Majorana* Microscope can be used for edge enhancement for biomedical samples such as cells and tissues to obtained detailed features. This system can also be helpful to detect disease such as cancer or tumors.

SC-*Majorana* system can also be applied as a hybrid mode-wavelength division multiplexer. This is achieved by exploring various wavelengths coming from SC and also the various polarizations coming from a q-plate, along the OAM modes carried by each polarization topology. This system can improve link capacity in wireless networks. The use of a q-plate in the system can make the achievement simpler because a q-plate is a tunable device controlled by external voltage, acting as a switcher.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

REFERENCES

[1] S. Mamani, D Nolan, L. Shi, R. Alfano, Special classes of optical vector vortex beams are Majorana-like photons, Optics Communication 464, 125425 (2020),

[2] S. Mamani, L. D, Nolan, R. Alfano, Majorana vortex photons a form of entangled photons propagation through brain tissue, J. Biophotonics (2019) e201900036.

[3] H. Nielsen, M. Ninomiya, Bosons being their own antiparticle in Dirac formulation, 2015, ArXiv: 1510.03932v1.

[4] F. Tamburini, B. Thidé, I. Licata, F. Bouchard, E. Karimi, Majorana states for subliminal structured photons, 2018, arXiv:1707.07160v4.

What is claimed is:

1. A method for imaging and deep imaging in a biological tissue sample or turbid media, the method comprising the steps of:
   transmitting Majorana photons through the biological tissue sample or turbid media, wherein the Majorana photons are a mixed state of spin angular momentum (SAM) and orbital angular momentum (OAM) (chiral entangled state), such beams having radial polarization and azimuthal polarization, thereby producing transmitted Majorana photons;
   receiving the transmitted Majorana photons with an optical receiver, thereby producing a received signal; and
   processing the received signal to produce a digital image of the biological tissue sample or turbid media, wherein SC-Majorana complex vortex beams (CVV) system and SC beam are used to detect and determine the size of small particles size 'a' of size μm and nm, using different wavelengths from SC in angle dependence and from ratio of Forward and Backward scatterings intensity.

2. A method for imaging and deep imaging in a biological tissue sample or turbid media, the method comprising the steps of:
   transmitting Majorana photons through the biological tissue sample or turbid media, wherein the Majorana photons are a mixed state of spin angular momentum (SAM) and orbital angular momentum (OAM) (chiral entangled state), such beams having radial polarization and azimuthal polarization, thereby producing transmitted Majorana photons;
   receiving the transmitted Majorana photons with an optical receiver, thereby producing a received signal; and
   processing the received signal to produce a digital image of the biological tissue sample or turbid media, wherein light 300 nm to 2500 nm is used to measure nano particles from 1 μm to 1000 μm from ratio of BS to FS and from angle of scatter $\theta=\mu/a$ where "a" is the size of a particle and $\lambda$ is the wavelength.

3. A method for imaging and deep imaging in a biological tissue sample or turbid media, the method comprising the steps of:
   transmitting Maiorana photons through the biological tissue sample or turbid media, wherein the Majorana photons are a mixed state of spin angular momentum (SAM) and orbital angular momentum (OAM) (chiral entangled state), such beams having radial polarization and azimuthal polarization, thereby producing transmitted Majorana photons;

receiving the transmitted Majorana photons with an optical receiver, thereby producing a received signal; and processing the received signal to produce a digital image of the biological tissue sample or turbid media, wherein an angular dependence of light scattering is used from small particles including micron size for pollen and water drops, and nanometer size virus (100 nm to 200 nm) using SC, UV lamp, LED, using a scattering angle equation $\theta = \lambda/a$.

* * * * *